(12) United States Patent
Thomke et al.

(10) Patent No.: US 7,806,623 B2
(45) Date of Patent: Oct. 5, 2010

(54) EXTERNAL FIXATION CLAMP

(75) Inventors: Roland Thomke, Bellach (CH); Vinzenz Burgherr, Bern (CH); Damian Fankhauser, Bern (CH)

(73) Assignee: Stryker Trauma S.A. (CH)

( * ) Notice: Subject to any disclaimer, the term of this patent is extended or adjusted under 35 U.S.C. 154(b) by 10 days.

(21) Appl. No.: 12/316,217

(22) Filed: Dec. 10, 2008

(65) Prior Publication Data
US 2009/0148232 A1    Jun. 11, 2009

Related U.S. Application Data

(62) Division of application No. 11/120,775, filed on May 3, 2005, now Pat. No. 7,491,008.

(30) Foreign Application Priority Data

Feb. 9, 2005   (EP)   ............................ 05100926

(51) Int. Cl.
    *E04B 1/26* (2006.01)
(52) U.S. Cl. ...................... 403/385; 403/344
(58) Field of Classification Search ................ 403/188, 403/316, 344, 373, 385; 606/54, 57
    See application file for complete search history.

(56) References Cited

U.S. PATENT DOCUMENTS

| 978,398 | A | * | 12/1910 | Rischard .................. 24/339 |
| 1,785,870 | A | | 12/1930 | Marles |
| 2,856,214 | A | | 10/1958 | Schrimshaw |
| 3,023,989 | A | | 3/1962 | White |
| 3,268,946 | A | * | 8/1966 | Case .......................... 403/188 |
| 3,466,712 | A | | 9/1969 | Behney |
| 3,767,235 | A | * | 10/1973 | Pitner ....................... 403/344 |
| 4,043,688 | A | | 8/1977 | Humlong |
| 4,310,209 | A | | 1/1982 | Fleming et al. |
| 4,707,051 | A | | 11/1987 | Hall |
| 4,772,153 | A | | 9/1988 | Huang et al. |
| 5,030,220 | A | | 7/1991 | Howland |
| 5,358,350 | A | | 10/1994 | Oertle et al. |
| 5,727,899 | A | | 3/1998 | Dobrovolny |
| 5,741,252 | A | | 4/1998 | Mazzio et al. |
| 5,752,954 | A | | 5/1998 | Mata et al. |

(Continued)

FOREIGN PATENT DOCUMENTS

DE    38 23 746 A1    1/1990

(Continued)

*Primary Examiner*—Victor MacArthur
(74) *Attorney, Agent, or Firm*—Lerner, David, Littenberg, Krumholz & Mentlik, LLP

(57) ABSTRACT

An insert for an external fixation has two jaws for clamping a rod-shaped element. The insert includes a locking element and is an angled piece having two free ends, with at least one engagement edge for engagement into the rod-shaped element being provided at its one free end. The insert has a recess or bore for engagement with a locking shaft of the clamp provided at the free end thereof that lies opposite to the free end having the rod engagement edge. The insert is angled so that it may extend through a passageway in one of the jaws and into a cavity formed in the jaw for receiving the rod. The insert rod engaging edges are tapered to bite into the rod to prevent its movement.

8 Claims, 15 Drawing Sheets

U.S. PATENT DOCUMENTS

| | | |
|---|---|---|
| 5,888,221 A | 3/1999 | Gelbard |
| 6,080,153 A | 6/2000 | Mata et al. |
| 6,340,361 B1 | 1/2002 | Kraus et al. |
| 6,342,054 B1 | 1/2002 | Mata |
| 6,616,664 B2 | 9/2003 | Walulik et al. |
| 6,692,177 B2 | 2/2004 | Crudele et al. |
| 6,702,814 B2 | 3/2004 | Walulik et al. |
| 7,491,008 B2 * | 2/2009 | Thomke et al. ............ 403/373 |
| 2004/0044344 A1 | 3/2004 | Winquist et al. |

FOREIGN PATENT DOCUMENTS

| | | |
|---|---|---|
| EP | 1522267 | 4/2005 |
| EP | 1661523 | 5/2006 |
| FR | 964114 | 8/1950 |
| GB | 2029490 | 3/1980 |

\* cited by examiner

EXTERNAL FIXATION CLAMP

CROSS-REFERENCE TO RELATED APPLICATION

This application is a divisional of U.S. application Ser. No. 11/120,775, filed on May 3, 2005, the disclosure of which is incorporated herein by reference.

BACKGROUND OF THE INVENTION

The invention relates to an insert for a clamping element for clamping a rod-shaped element of an articulated connection, particularly for a clamping element of an articulated connection for stabilizing bone fractures. Furthermore, the invention relates to an articulated connection having two clamping elements and having a locking element. In particular, the invention relates to an insert for optimizing the fixation of round rods in an external fixation system.

An articulated connection is known from U.S. Pat. Nos. 5,741,252, 5,752,954, 6,080,153, 6,342,054, 6,616,664, and 6,702,814, respectively, which consists of two or four individual clamping jaw elements and a central shaft or screw. In the case of this articulated connection, it is possible to introduce one or two rod-shaped elements into the corresponding cavities from the side. In U.S. Pat. No. 5,752,954, a spring is disposed between the two center clamping jaw elements, and it is possible to clip the rod-shaped elements in, counter to its spring force, and thereby hold the articulated connection in place against the rod-shaped elements, before it is locked in position. In U.S. Pat. No. 6,616,664, narrow lever arms disposed on the side are provided, in order to hold rod-shaped elements that have been inserted from the side in place before the articulated connection is locked in position.

These known articulated connections are particularly used with frame-type systems for external treatment of bone fractures, also referred to as external fixators. By means of a suitable material pairing of the clamps of the articulated connection and of the rods, for example steels of different hardness or a combination of steel and aluminum, or also by means of suitable surface structures of the interior surface of the clamp and the mantle surface of the rod, the result can be achieved that the rod-shaped elements are sufficiently secured against rotation and axial displacement after the locking screws have been fixed in place.

It is desirable to construct such external fixators using non-metallic materials, for example plastic materials, particularly in order to achieve a weight reduction of such a system. If the modules or parts of such a clamp are made of plastic injection-molded materials, there may be the difficulty in finding suitable material pairings with which sufficient fixation can be achieved. This is a problem particularly because many plastics are characterized by negative creep behavior, which causes connections that have been tightened to gradually come loose, i.e. to lose their gripping power.

Another problem that arises with such configurations is the high pressure stress on the plastic parts when the screw connection has been tightened, and this stress can result in stress cracks due to irregular stress on the plastic structure. This is particularly dangerous because such defects only occur after a certain period of time, and are not clearly evident optically.

BRIEF SUMMARY OF THE INVENTION

It is an aspect of the present invention to provide an insert for a clamping element that allows insertion of rod-shaped elements from the side, and whereby the clamping element, used double, can be inserted directly as an articulated connection, whereby the aforementioned elements of the clamping element can consist of a non-metallic material, for example plastic, without any impairment of the safety of the resulting articulated connection in an external fixator.

Furthermore, it is an aspect of the present invention to provide a simple clamping element designed for use of such inserts.

Yet another aspect of the invention is an improved articulated connection.

It is one goal of the invention to offer a suitable system that allows an optimal and, to the greatest extent possible, a direct friction lock between the connecting clamp and the rod-shaped elements, which remains constant. At the same time, the locking does not result in overly great stress on the plastic parts and therefore helps to prevent structural damage. The permanent stability of frame configurations for external fixators, which are predominantly made of plastic, is guaranteed, in other words the reliability known from previous metal designs is assured. Furthermore, this design should be a design that can be easily produced and advantageously assembled, in order to obtain a relatively inexpensive product.

These and other aspects of the present invention are accomplished by a clamping element for engaging a rod of an external fixation system. The clamping element has a first jaw member having a bore therethrough and a rod receiving cavity spaced radially from the bore. The cavity may be part cylindrical shape extending along an axis. The clamp includes a second jaw member having a bore therethrough and a rod receiving cavity spaced from the bore. A locking shaft extends through the bores of the first and second jaw members in a direction generally perpendicular to the axes of the cavities in the jaw members. The locking shaft may be threaded at one or both ends to allow for the tightening of the clamping elements against the rod. The clamping element includes an insert having a first part with a bore or recess for receiving the locking shaft and a second part extending into the rod receiving cavity of at least one of the jaw members. The second part has a tapered or pointed edge for engaging an outer circumferential surface of the rod received within the cavities of the first and second jaw members. Once the jaws are tightened by the use of the locking shaft and any associated threaded locking element coupled thereto the tapered edge bites into the outer surface of the rod fixing it axially within the cavities. In addition, the insert takes part of the load clamping the rod between the jaw members.

The insert may be either angled or L-shaped. The first part of the L-shaped including a bore for receiving the locking shaft with the second L-shaped portion extending through a passageway in at least one of the jaw members and into engagement with the cavity housing the rod. The tapered edge of the insert may be in the form of a plurality of points or may have a roughened surface for better biting into and engaging the rod and preventing its motion. The tapered engagement edge can extend both axially along the rod and perpendicular thereto to better prevent axial motion of the rod within the cavity. The insert may include an anti-rotation feature to prevent the insert from rotating out of alignment with the axis of the cavity. This can be accomplished by having a portion of the insert in the region of the bore engaging the locking shaft or a portion of the insert engaging a recess in the jaw member. Preferably, the passageway runs from the outside of the jaw member through the jaw member in a direction that is perpendicular to the axis of the cavity and through a surface that delimits the cavity so that the first part of the insert clamp can lie against the clamp outer surface with the second part extending generally at 90° thereto extending into the cavity which receives the rod. In a preferred embodiment of the outer side of the jaw with the insert has a recess extending along the face of the jaw member and recessed in the direction of the passageway to receive the first part of the jaw. The recess is sized to receive the first part of the insert as a press-fit so that the insert is retained on the outer side of the jaw member and is prevented from rotation with respect thereto. Also in the preferred embodiment the bore in the first part for receiving the locking shaft may be oblong so that the jaw member with the insert press-fit therein can be moved apart when a rod-shaped element is inserted in a direction perpendicular to the axis of the cavity. In a second embodiment the jaw member may have a beveled surface for engaging a beveled surface on the insert to provide support for the insert when engaging the rod.

In particular, an insert according to the invention allows a direct transfer of force from the screw or another locking element to the rod, in order to relieve stress on the plastic component.

In other embodiments, it is also possible to achieve the inserts as extrusion-coated parts. In this case, metallic parts are laid into the injection-molding mold and then coated with plastic by extrusion coating. This is a common technique, but it requires a complicated and accordingly expensive production process (robot-controlled placement of the metal parts or manual placement). A disadvantage of such a solution is that extrusion-coated parts are also subject to the creep phenomena mentioned.

BRIEF DESCRIPTION OF THE DRAWINGS

The invention will now be explained in greater detail, making reference to the drawings, using exemplary embodiments. These show.

DETAILED DESCRIPTION

Figure 1:
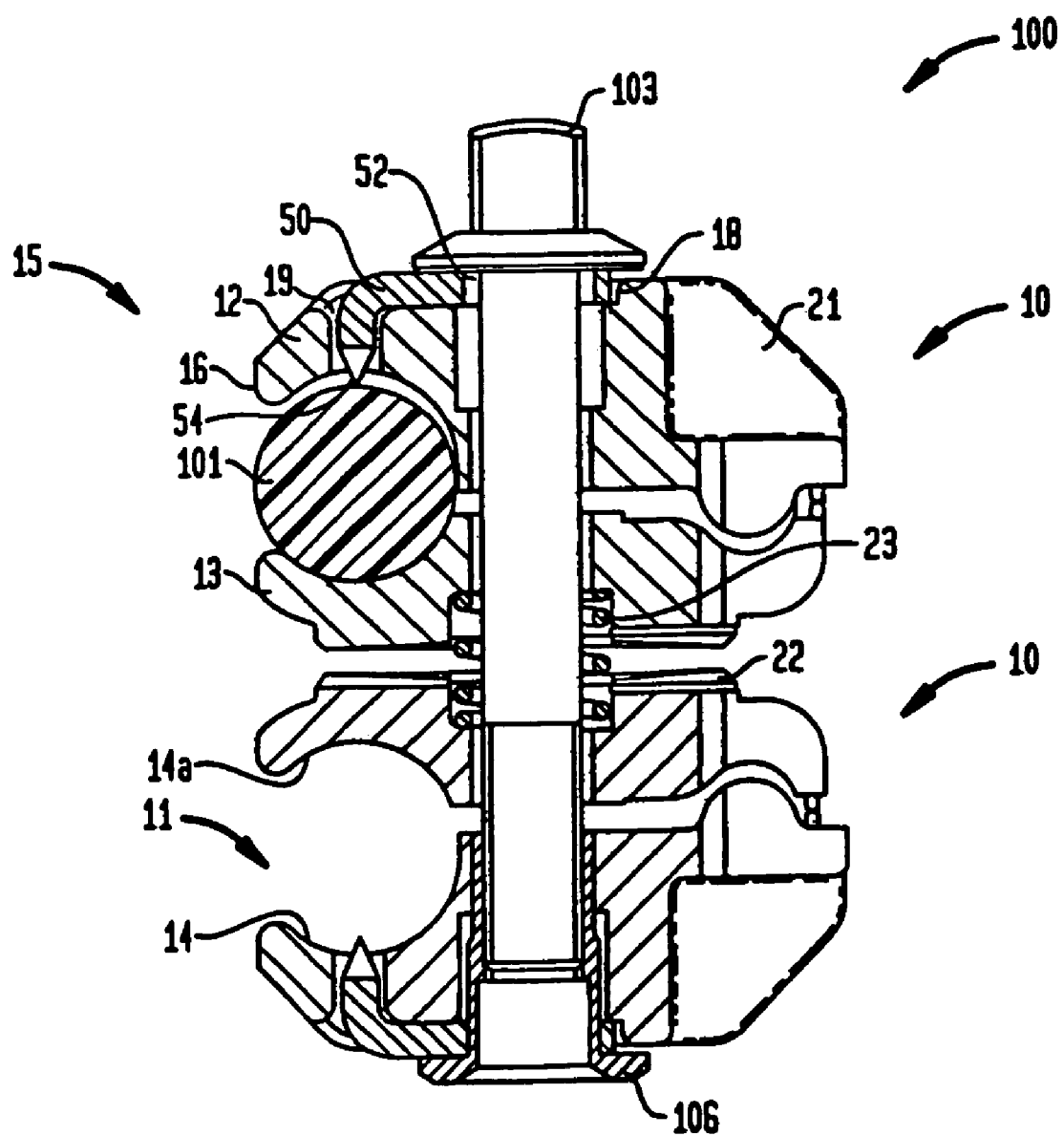
FIG. 1 is a cross-sectional side view of an articulated connection having two clamping elements having inserts according to a first exemplary embodiment of the invention.

Referring to FIG. 1 there is shown a cross-sectional side view of a preferred articulated connector 100 having two clamping elements 10 having inserts 50 according to a first exemplary embodiment of the invention.

Each clamping element 10 has two clamping jaws 12 and 13 that lie opposite one another and have a cavity 11 for accommodating a rod-shaped element 101. Rod 101 may be formed of a polymeric or composite material such as carbon fiber reinforced PEEK. The clamping jaws 12 and 13 have a groove with a longer curvature portion 14 and having a short curvature portion 14a that runs crosswise, in each instance, at their free ends 15, which grooves together define the cavity 11. At the free ends 15, the outer edges 16 of the sides of the clamping jaws 12 and 13 that face one another are rounded, in order to facilitate the insertion of a rod-shaped element from the side. Opposite the cavity 11 and the free ends 15, a hinge means 17 is provided, which can be seen in FIG. 2, and which connects the clamping jaws 12 and 13 with one another to form a single piece. A screw 103 that passes through clamping elements 10 and can be screwed into a nut 106 closes the articulated element 100, and locks rods 101 that can be inserted into the latter in place. This screw/nut connection is a locking element that can also be implemented by way of levers and other elements.

Clamping elements 10 have a solid cross-section in their center region, forming two lateral cross-ribs 21, which are particularly marked in the upper region of clamping jaw 12. The region between cross-ribs 21 is recessed towards the front edge 16, with the exception of a rectangular insert accommodation or recess 18 that can be seen in the top view of FIG. 2. Insert accommodation 18 has a continuous bore centrally in the clamping element 10, to accommodate screw 103. Ribs 21 can also run completely on the outside of the clamping element, depending on the width of an insert 50. Insert accommodation 18 can also consist of a second step, at a distance from ribs 21.

In the inner or lower clamping jaw 13, cross-ribs 21 end in a ring flange 22, which can have a flat, recessed, ring-shaped segment, for example, which can be followed by a recess that saves weight and material and is advantageous for injection-molding production, in the center of which a bore is provided. This continuous bore is oriented to align with the aforementioned continuous bore in the upper clamping jaw 12. In the clamping element 10, it runs perpendicular to the axis of the cavity 11 and parallel to the back of the hinge means 17. However, it could also run at a slant. The ring flange 22 can be a carrier of engagement elements such as radial teeth, in order to prevent rotation of the clamping elements 10 relative to one another. A separate rotation element for insertion between the two clamping elements 10 can also be provided.

In the representation of FIG. 1, preferred articulated element 100 is formed from two clamping elements 10. The clamping elements 10 are provided, for example, for a rod having a diameter of 12 millimeters, for example. Then, the opening at the free ends has a diameter of 8 millimeters, for example, in the resting state. If the upper clamping element 10 is now supposed to be provided for a rod having a diameter of 4 to 6 millimeters, then the opening at the free ends 15 would have a diameter of 2 millimeters, for example, in the resting state.

In the preferred embodiment an insert 50 is inserted into insert accommodation or recess 18; the former consists of an L-shaped profile that will be described in greater detail in FIG. 3 and others. A continuous slit bore 19 is provided in upper clamping jaw 12, in insert accommodation 18, through which the tips of the L-shaped profile of insert 50 can project, into the region of the cavity 11; slit bore 19 ends in groove 14, preferably in the center of groove 14. They can always project into the groove 14 by 1 millimeter, for example, because the profile surface of the insert 50 sits in the clamping jaw with a press fit.

Figure 2:
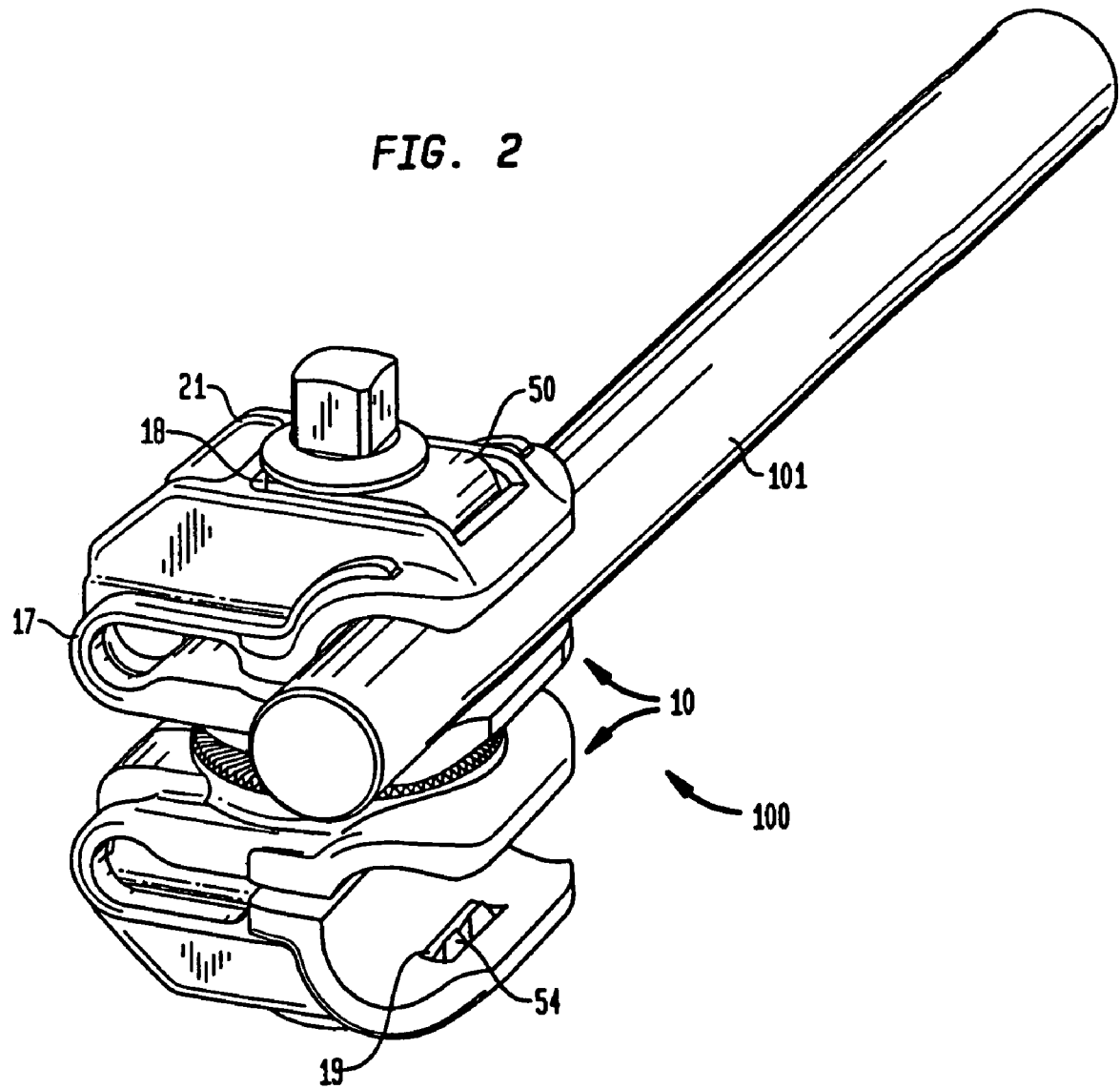
FIG. 2 is a perspective view of the first exemplary embodiment according to the invention, with an inserted rod.

FIG. 2 shows a perspective view of the first embodiment according to the invention, with an inserted rod 101. The same characteristics in the drawings are shown with the same reference symbols, in each instance. In lower clamping element 10, the break-through of slit bore 19 and two teeth of lower insert 50, which is held by the nut 106, can be seen. Here, the connection between clamping elements 10 is pressed apart by way of a pressure spring 23 that has been inserted between them.

Figure 3:
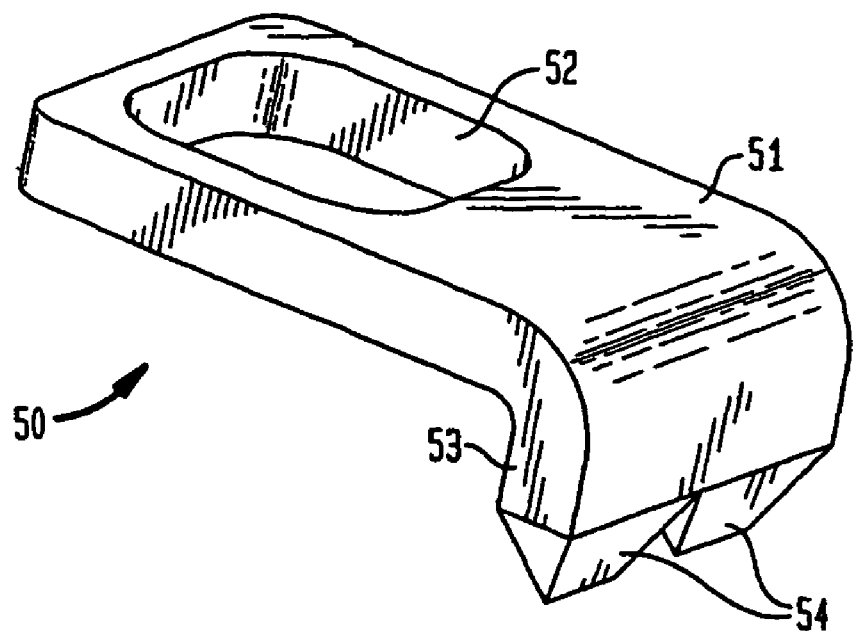
FIG. 3 is a perspective view of the insert according to the first exemplary embodiment.
Figure 4:
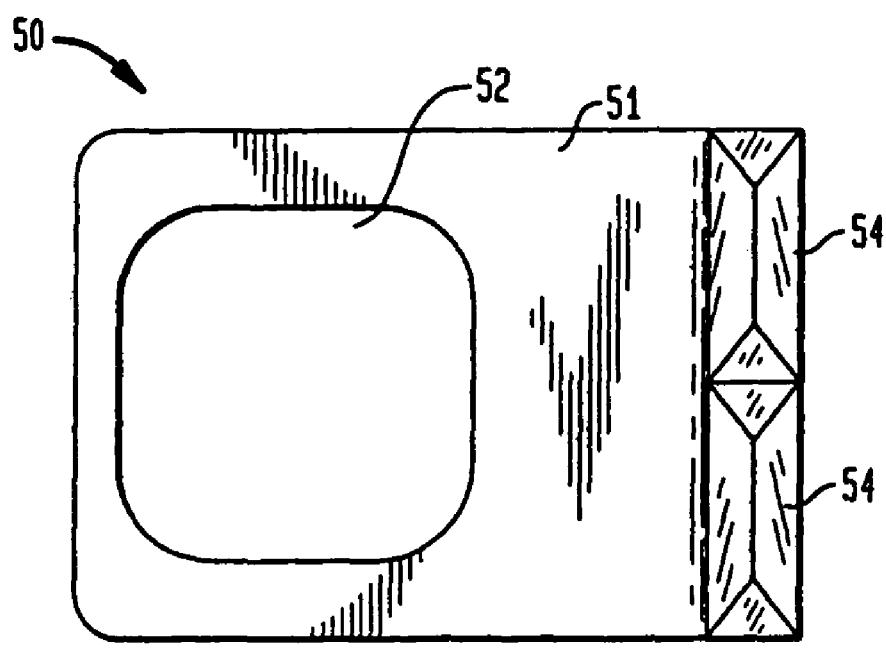
FIG. 4 is a bottom view of the insert according to FIG. 3.
Figure 5:
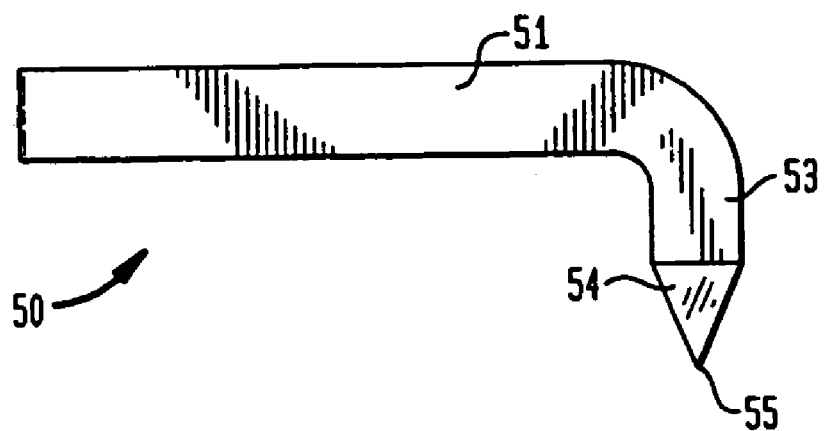
FIG. 5 is a side view of the insert according to FIG. 3.

FIG. 3 shows a perspective view of insert 50 according to the first embodiment, FIG. 4 shows a bottom view of this insert 50, and FIG. 5 shows a side view of the insert 50. In the top view, the insert 50 is essentially a rectangular plate having an oblong bore 52. In cross-section, the insert 50 looks like an L-shaped small plate having a long side 51 and a shorter engagement side 53. Here, the free end of the shorter engagement side 53 ends in two teeth 54, which have a prism shape in cross-section. The insert 50 serves as an inserted part in the plastic part of clamping element 10, which is placed into the coupling element 10 under screw head 103 or under nut 106, respectively. Preferably, here insert 50 is a die-punched part. In this embodiment, metal part 50 is affixed to the outside of the articulated element 100, making reference to FIGS. 1 and 2. Insert 50 is structured in such a manner that it can claw directly into a round rod-shaped element 101, through the penetration or slit bore 19 in the clamping element 10, with an angled front side 53, and thereby results in a material deformation or notching in round-shaped element 101. As a result, an optimal friction lock between elements 10 (by way of insert 50) and a rod 101 is achieved. The advantage is, in particular, that the friction lock comes about directly between screw 103 (or nut 106) and rod-shaped element 101, by way of insert part 50, and plastic component 10 of coupling element 100 now serves only as a guide element. As a result, the stress on it is significantly relieved, and it can be optimally designed for this guide function. In this context, engagement edge 55 of teeth 54 is directed essentially axially in the direction of rod 101, and prevents rotation in particularly excellent manner.

Figure 6:
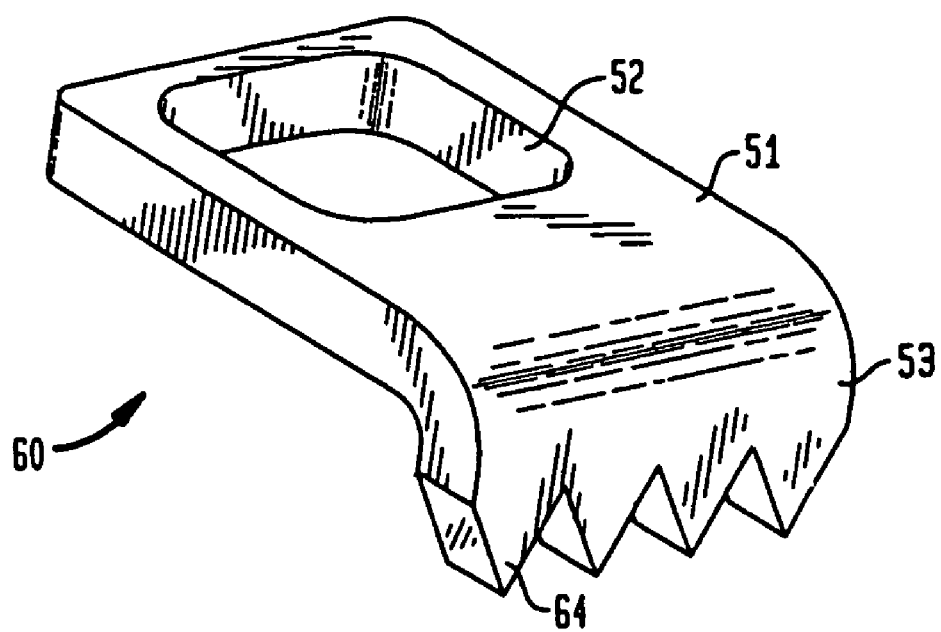
FIG. 6 is a perspective view of an insert according to a second exemplary embodiment.
Figure 7:
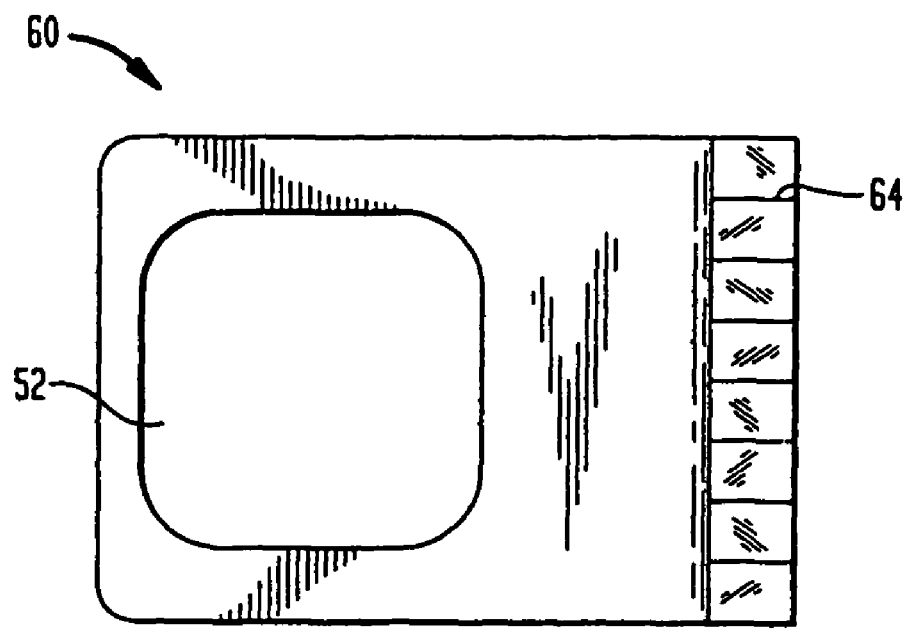
FIG. 7 is a bottom view of the insert according to FIG. 6.
Figure 8:
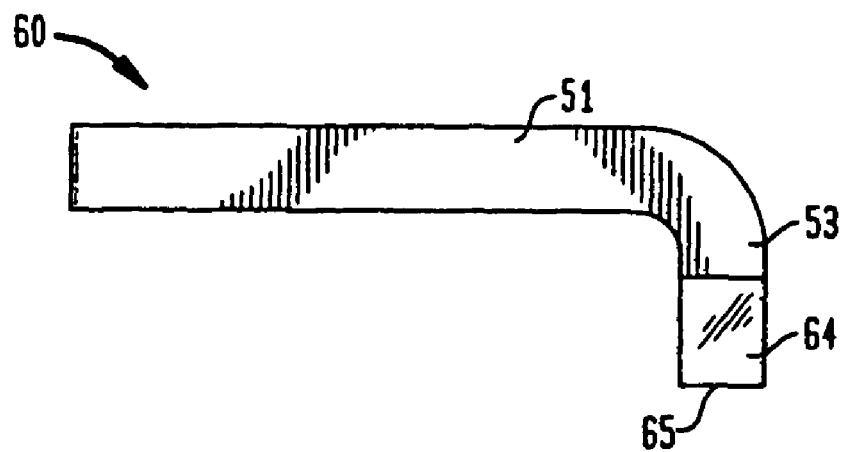
FIG. 8 is a side view of the insert according to FIG. 6.

FIG. 6 shows a perspective view of an insert 60 according to a second embodiment. FIG. 7 shows a bottom view of the insert 60 according to FIG. 6, and FIG. 8 shows a side view of the insert 60 according to FIG. 6. The insert 60 is essentially very similar to insert 50, with the difference that here, four teeth 64 are provided, and that the engagement edge 65 of the teeth 64, in each instance, stands crosswise to the longitudinal direction of rod 101, into which it can engage. Therefore the engagement edge 65 of the teeth 64 stands essentially crosswise to the direction of rod 101 and prevents axial displacement of the clamping element 10 on rod 101, in particularly excellent manner.

Figure 9:
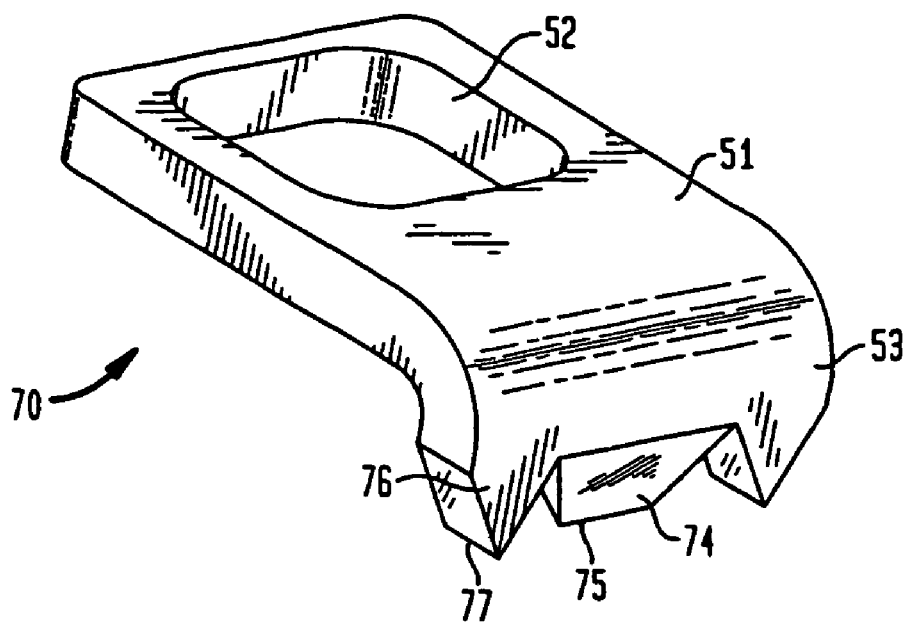
FIG. 9 is a perspective view of an insert according to a third exemplary embodiment.
Figure 10:
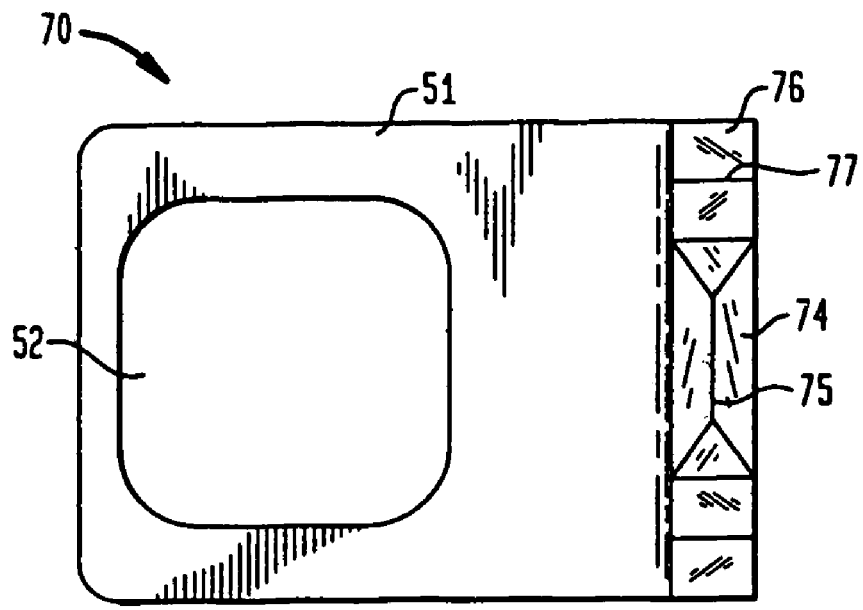
FIG. 10 is a bottom view of the insert according to FIG. 9.
Figure 11:
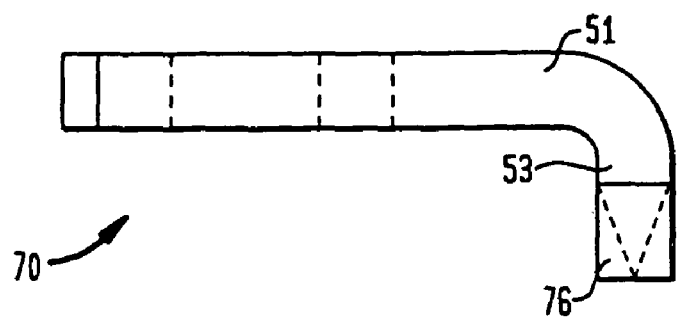
FIG. 11 is a side view of the insert according to FIG. 9.

FIG. 9 shows a perspective view of on insert 70 according to a third exemplary embodiment, FIG. 10 shows a bottom view of the insert according to FIG. 9, and FIG. 11 shows a side view of the insert according to FIG. 9. In this embodiment variant, the first and second exemplary embodiments are combined, in principle. The insert 70 has lengthwise teeth 74 having an engagement edge 75 that prevents rotation, and crosswise teeth 76 having an engagement edge that prevents axial displacements. Here, one central lengthwise tooth 74 and two crosswise teeth 76 disposed to the sides of the former are provided; two or more lengthwise teeth 74 and one crosswise tooth 76 on only one side, or, in advantageous manner, two or more crosswise teeth 76, symmetrically, could be provided. It is essential in this exemplary embodiment that the teeth 74 and 76, respectively, are oriented at a right angle to one another, in order to reliably prevent both lengthwise displacement of the rods 101 and their rotation.

Figure 12:
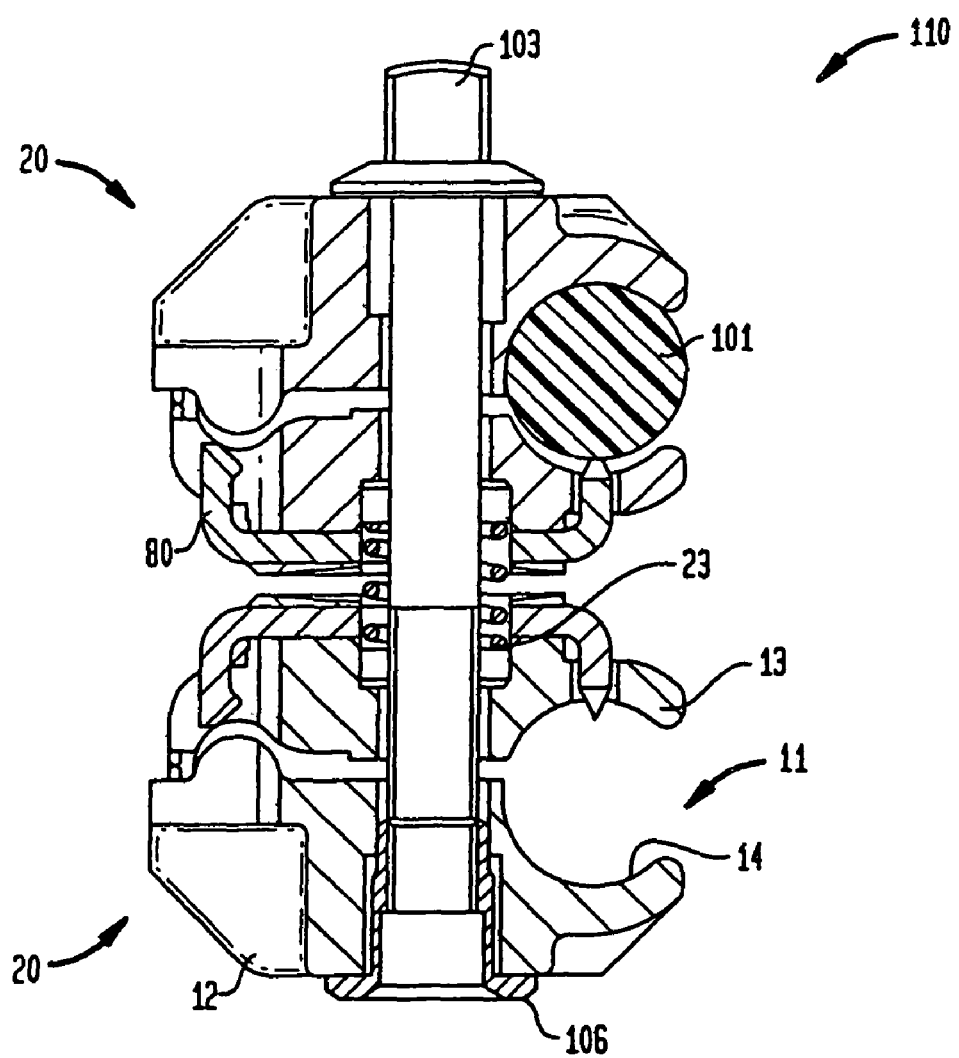
FIG. 12 is a cross-sectional side view of an articulated connection having two clamping elements having inserts according to a fourth exemplary embodiment of the invention.
Figure 13:
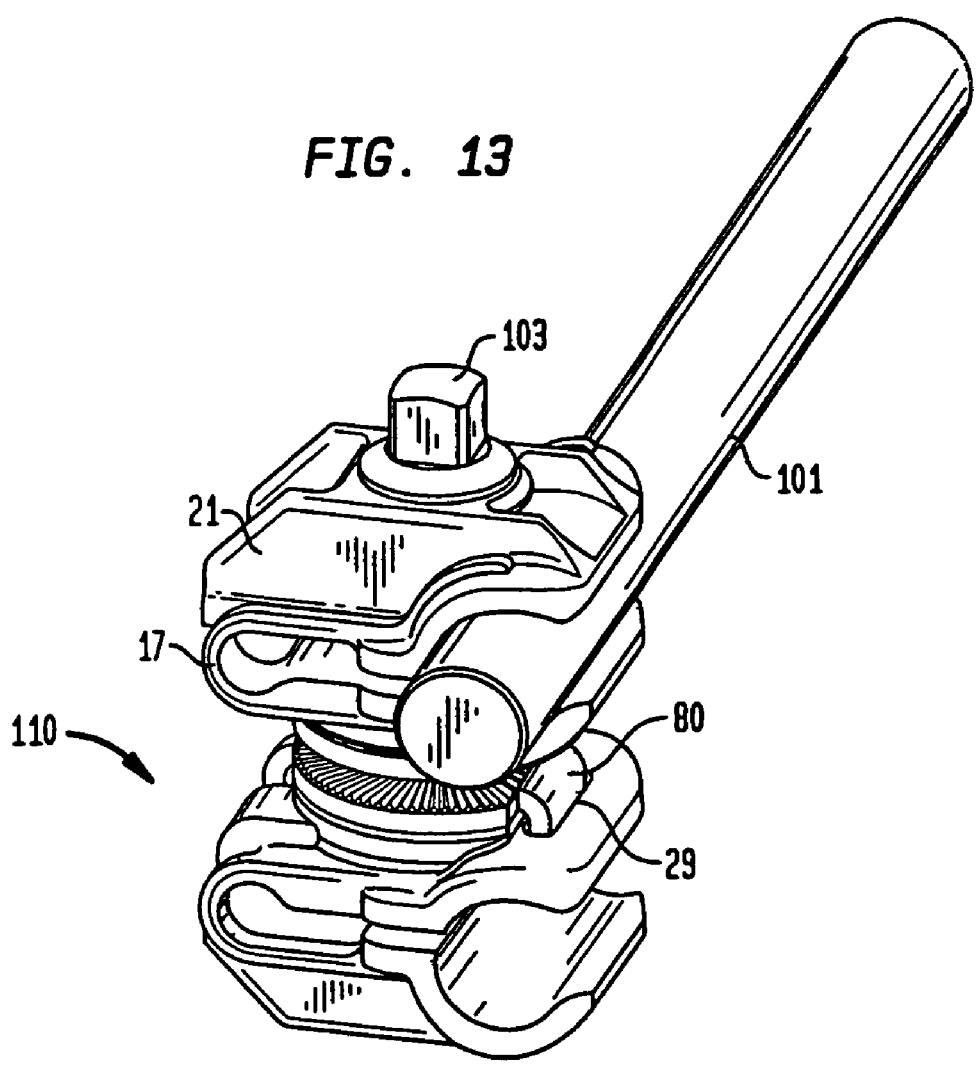
FIG. 13 is a perspective view of the articulated connection according to FIG. 12, with an inserted rod.
Figure 14:
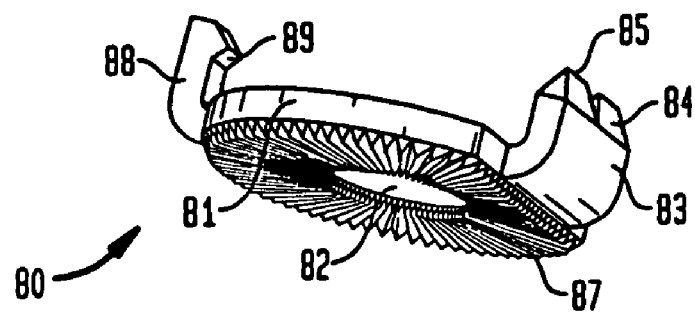
FIG. 14 is a perspective view of the insert according to the fourth exemplary embodiment.
Figure 15:
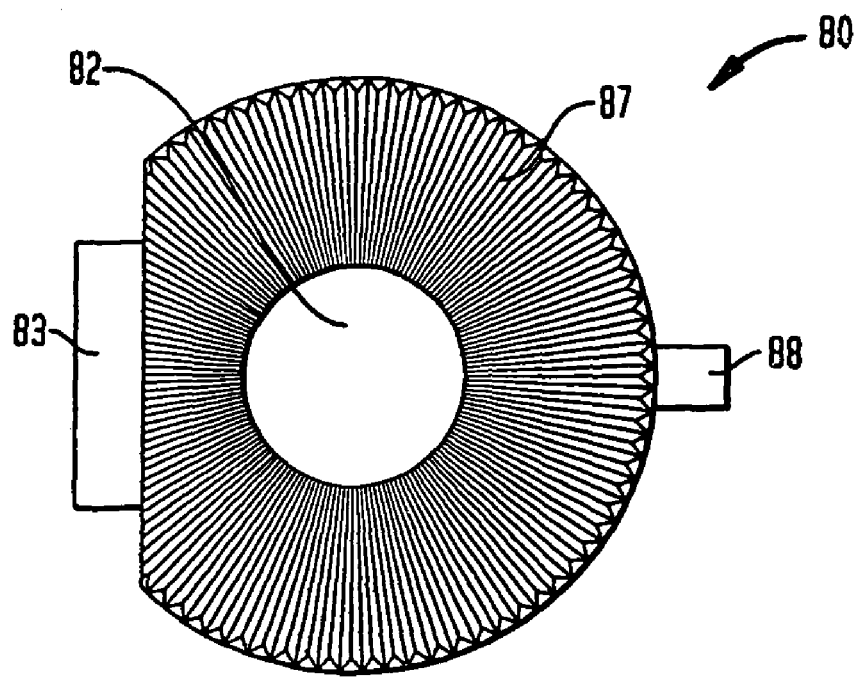
FIG. 15 is a bottom view of the insert according to FIG. 14.
Figure 16:
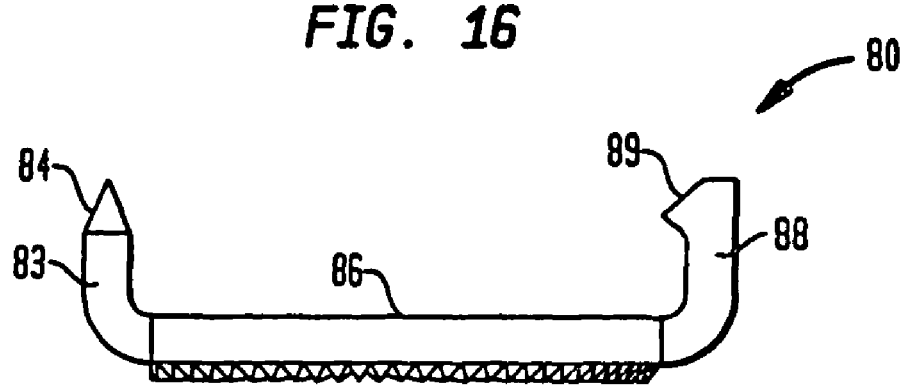
FIG. 16 is a side view of the insert according to FIG. 14.
Figure 17:
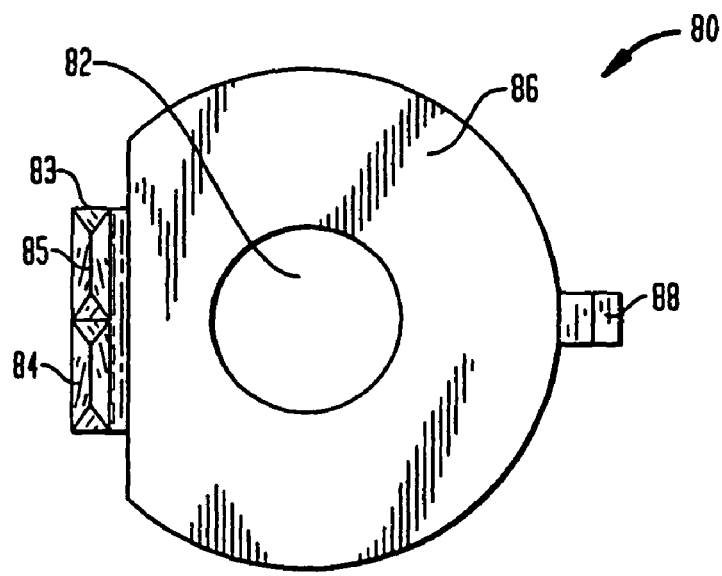
FIG. 17 is a top view of the insert according to FIG. 14.

FIG. 12 shows a cross-sectional side view of a second articulated connection 110 having two clamping elements 20 having inserts 80 according to a fourth embodiment of the invention, and FIG. 13 shows a perspective view of this fourth embodiment according to the invention, with an inserted rod 101. The clamping elements 20 correspond to a second embodiment of clamping elements as compared with clamping elements 10, since they have been appropriately modified to accommodate the inserts 80, which will be described in connection with FIG. 14 to 17. FIG. 14 shows a perspective view of insert 80 according to the fourth embodiment, FIG. 15 shows a bottom view of it, FIG. 16 shows a side view, and finally, FIG. 17 shows a top view of insert 80 according to FIG. 14.

The lower clamping jaw 13 has a flat contact surface on its underside, on which the inner side 86 of the insert 80 rests (in contrast to the riffled or serrated flange 22 shown in FIGS. 1 and 2).

Furthermore, the clamping element 20 has a slit bore 29 that corresponds to slit bore 19, and opens into groove 14 of clamping jaw 13, analogously. The insert 80 is structured in U shape, and, similar to insert 50, has a plate surface 81 that is configured here to be round, and is flattened on the side of the engagement side 83. In the embodiment shown, two teeth 84 having engagement edges 85 which may be tapered to a pointed edge, are provided. It is clear that other configurations corresponding to the above second and third exemplary embodiments can also be implemented.

On the side lying opposite the engagement side 83, a locking bar 88 is provided, which runs essentially parallel to the engagement side 83. The locking bar 88 runs in a slit of clamping elements 20 that runs parallel to the bore that accommodates the screw, and has a locking projection 89 that can press into the material of clamping element 20 in the depth of the slit.

In this embodiment variant, two inserts 80 come to rest on one another directly, between the two parts of the clamping elements 20, which are made of plastic, for example, and additionally take on the function of a rotation lock 87 of clamping elements 20. In this case, the plastic parts do not have any teeth on the underside. Preferably, the insert is produced as a die-punched part. The radial teeth of rotation lock 87 engage into one another when the screw 103 is tightened, and, in order to improve the rotation lock, the insert additionally has a locking bar 88 that engages into clamping jaw 13 of plastic part 20.

In addition, this insert 80 can be configured with hooks 89 and engagement side 83, as a clip or snap, and this simplifies assembly, since the parts can thereby be clicked onto the clamping element 20. In this variant, as well, the teeth that engage in the rods 101 can be configured in the most various forms, of which the exemplary embodiments shown only form an advantageous selection. For example, round conical points can also be provided, instead of teeth 54, 64, 74, 76, 84, or in addition to them. These are engagement elements, in each instance. Any such means that can be referred to as a means for generating high friction forces can be viewed as being an engagement element. This can simply have a rough surface, one or very many carpet-like little points can be present, or the engagement element can assume other embodiment forms mentioned in the specification and in the claims.

Figure 18:
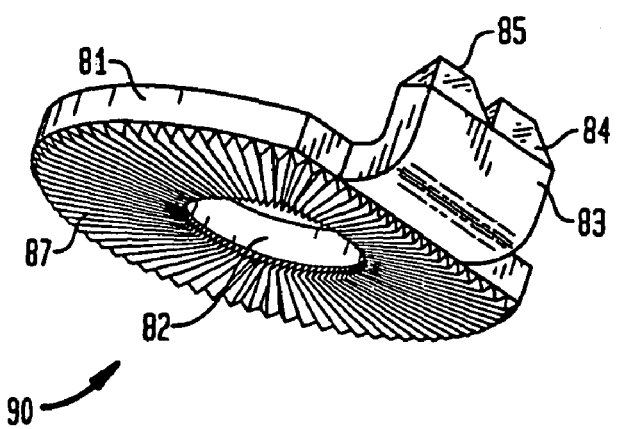
FIG. 18 is a perspective view of the insert according to a fifth exemplary embodiment.
Figure 19:
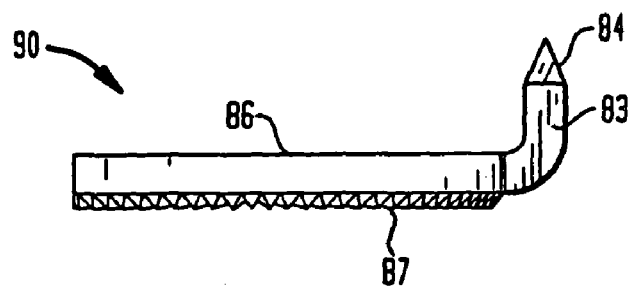
FIG. 19 is a side view of the insert according to FIG. 18.

FIG. 18 shows a perspective view of an insert 90 according to a fifth embodiment, and FIG. 19 shows a side view of this insert 90 according to FIG. 18. The only difference between the fourth and the fifth embodiment is that the insert 90 does not have a locking bar 88. Therefore the teeth 84 that claw into rods 101 when the articulated element is fixed in place are the only elements that simultaneously prevent rotation of the plastic clamps 10 and 20. Therefore the rotation lock 87 is secured only on one side, and particularly utilizes the positive lock in the slit bore 29 only asymmetrically.

It is clear that insert 50 according to the first embodiment can also be equipped with a locking bar 88, if a corresponding recess is provided in clamping jaw 12.

It is directly evident that two inserts 80 and 90, respectively, provided for the inner clamping jaws 13, have a round bore 82, while the inserts 50, 60, and 70, respectively, provided for the outer clamping jaws 12, have rectangular bores or oblong bores. This is due to the fact that in order to insert the rods 101, the clamping jaws 12 and 13 must be pressed apart. In doing so, clamping jaws 12 move about a pivot point of hinge part 17 and thereby relative to screw 103 or nut 106, thereby making it necessary for a corresponding clear space to be present for the path of the screw 103 or nut 106. Instead of the closed bore, a U-shaped slit can also be provided, which at least partially surrounds a clamping element 103, 106.

Figure 20:
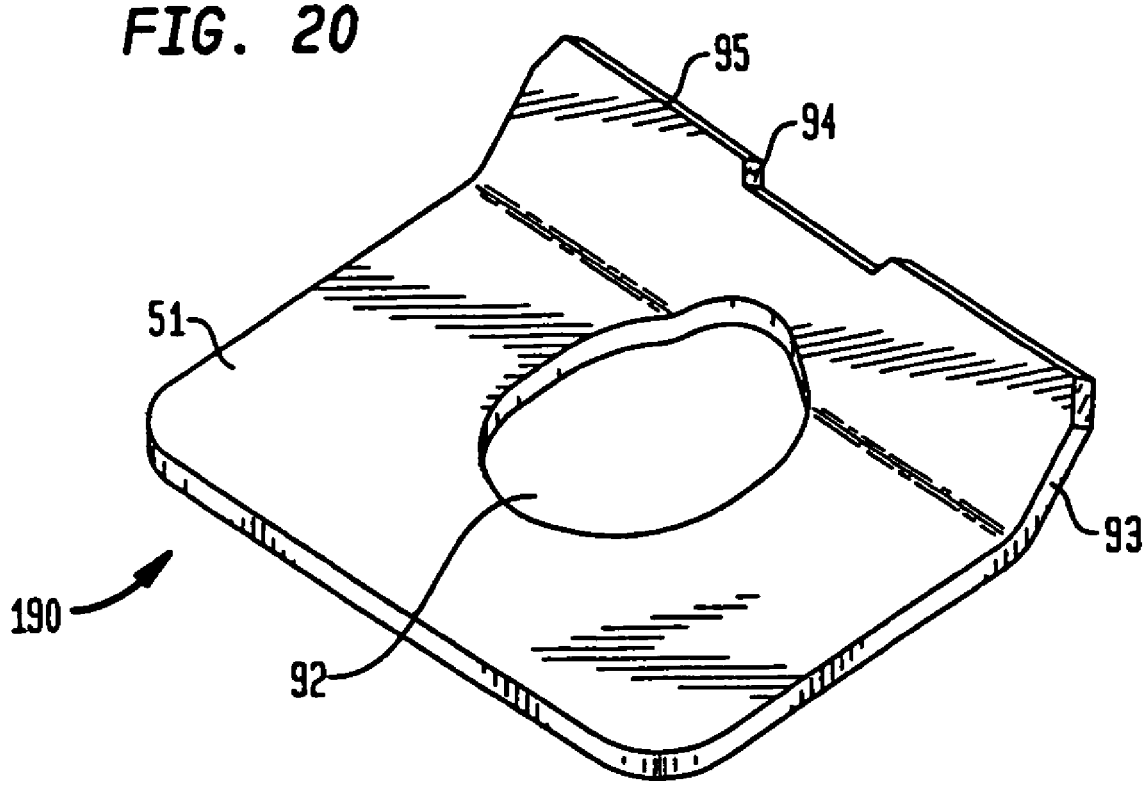
FIG. 20 is a perspective view of the insert according to a sixth exemplary embodiment.
Figure 21:
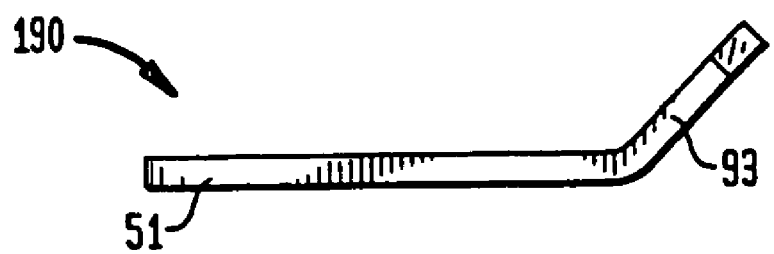
FIG. 21 is a side view of the insert according to FIG. 20.
Figure 22:
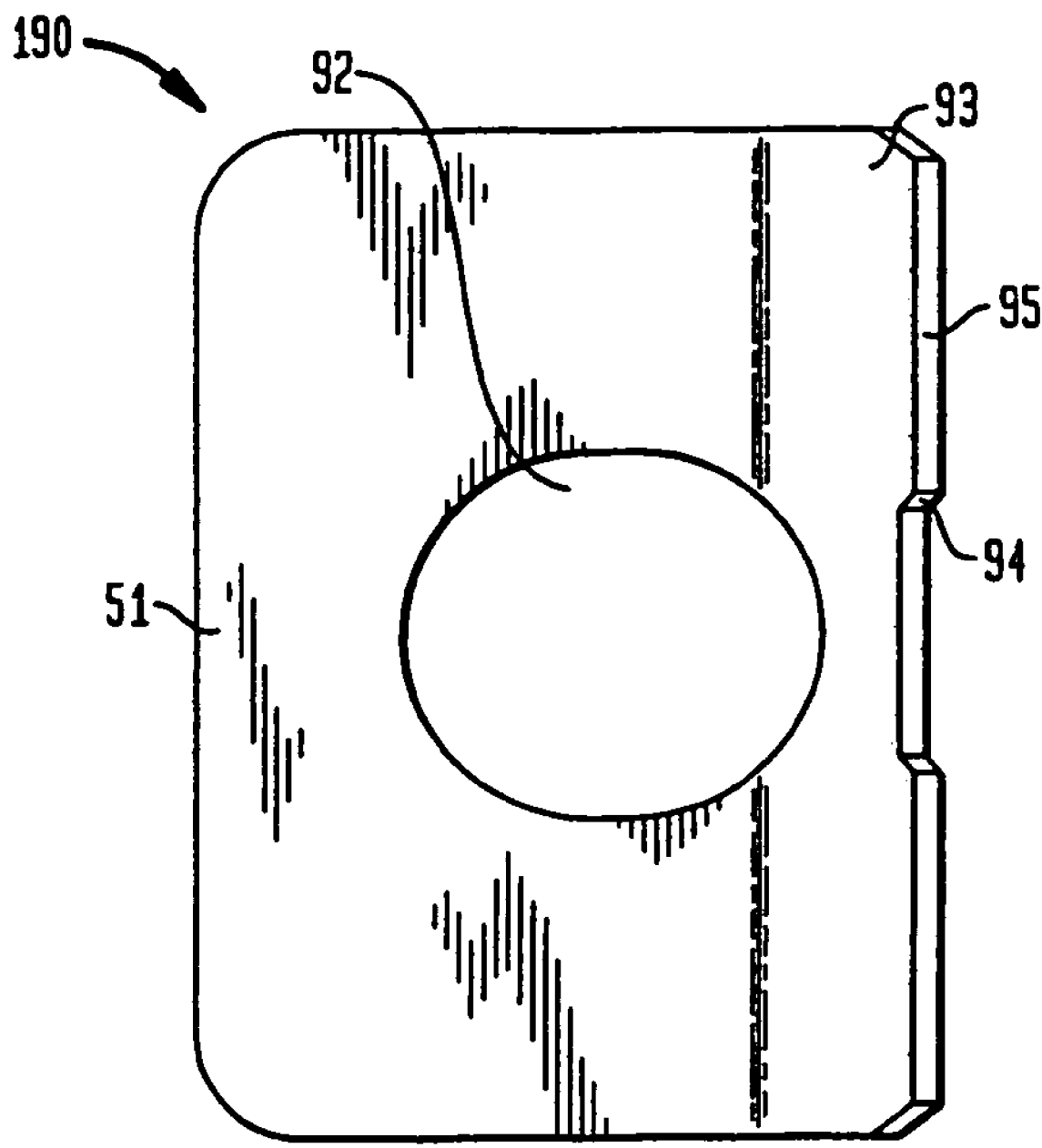
FIG. 22 is a bottom view of the insert according to FIG. 20.

FIG. 20 shows a perspective view of an insert 190 according to a sixth embodiment. FIG. 21 shows a side view of the insert 190 according to FIG. 20, and FIG. 22 shows a bottom view.

Insert 190 is configured to be rectangular with rounded corners, and, similar to insert 50, has a plate surface 51 that makes a transition into the engagement side 93 on one side, at a slant. This can be achieved by means of punching, for example. The angle between the surface 51 and the engagement side 93 can be 45 degrees, for example, but other values, advantageously between 30 and 60 degrees, are also possible. An oblong hole 92 is disposed in the surface 51; its longitudinal direction is oriented perpendicular to the punch line of the engagement side 93. The smaller diameter of the oblong hole 92 essentially corresponds to the diameter of the screw 103 provided for the clamping element 30 according to FIG. 23. Oblong hole 92 has a region that extends into the slant of the engagement side 93. This is advantageous because in this way, in the case of the clamping element 30, groove 14 for rod 101 can be brought closely up to screw 103, which runs crosswise. The region of the engagement side 93, which is thereby shortened, is advantageous since two rods 101 are thereby rigidly coupled with one another, tightly, by way of screw 103, and little load acts on the clamping elements 30 that compose the articulated element 120.

In the exemplary embodiment shown, two lateral teeth 94 are provided with engagement edges 95. This can also be described as an engagement edge 95 that is set back in the center region. It is clear that other engagement configurations, in accordance with the above first through fifth exemplary embodiments, can also be implemented.

On the side lying opposite the engagement side 93, no locking bar is provided here, which would run perpendicular to the surface 51. Such a locking element, similar to the locking bar 88, is, of course, possible, in order to support the locking effect.

In this embodiment variant, the two inserts 190 come to rest directly between the two clamping jaws 12 and 13 of each clamping element 30. For this purpose, the clamping jaw 12 has a bevel 38 that can rest against the engagement side 93. In this context, the screw 103 passes through the opening 92, which is configured as an oblong hole, in order to allow a movement of insert 190 crosswise to the orientation of rod 101.

Figure 23:
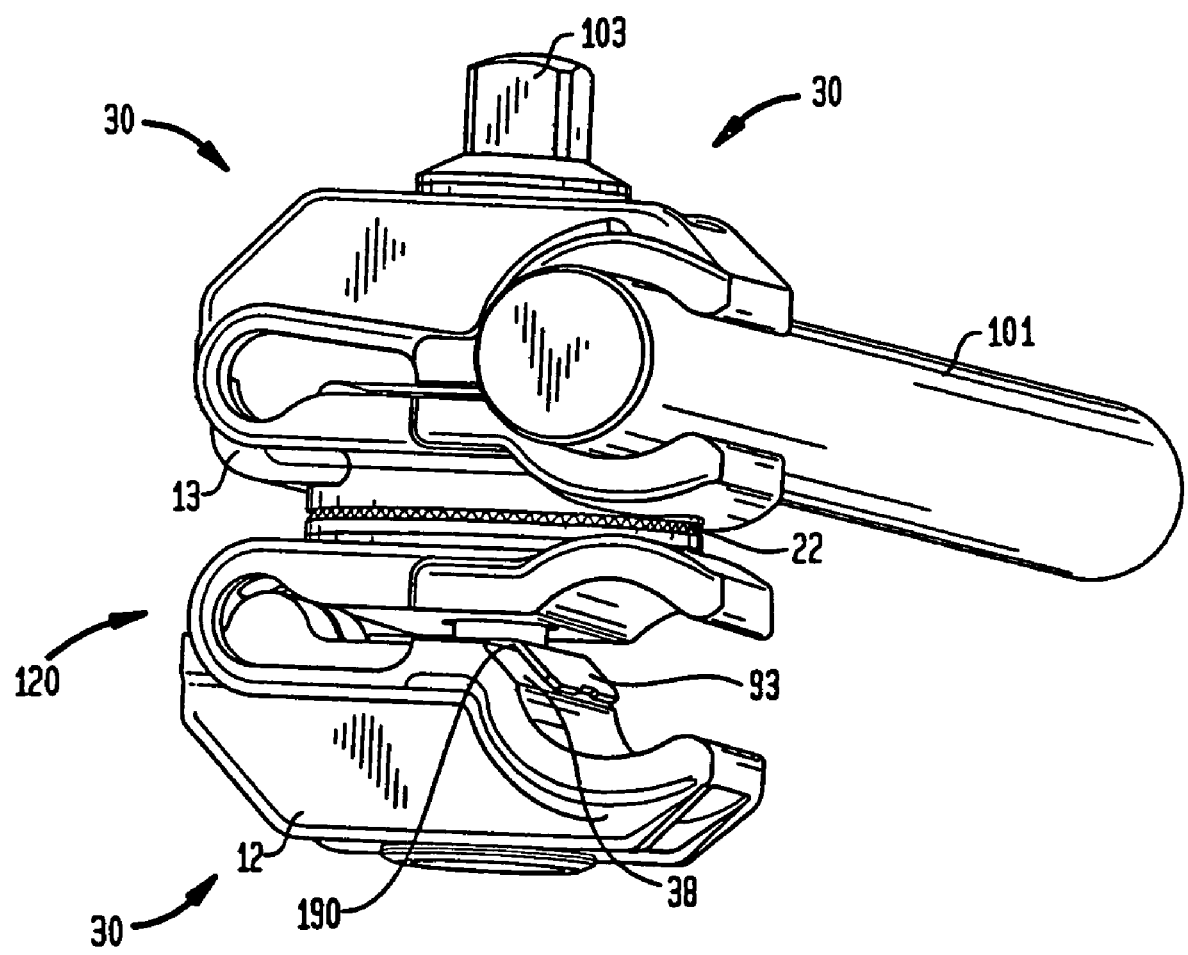
FIG. 23 is a perspective view of an articulated connection having inserts according to the sixth exemplary embodiment of the invention, with an inserted rod.
Figure 24:
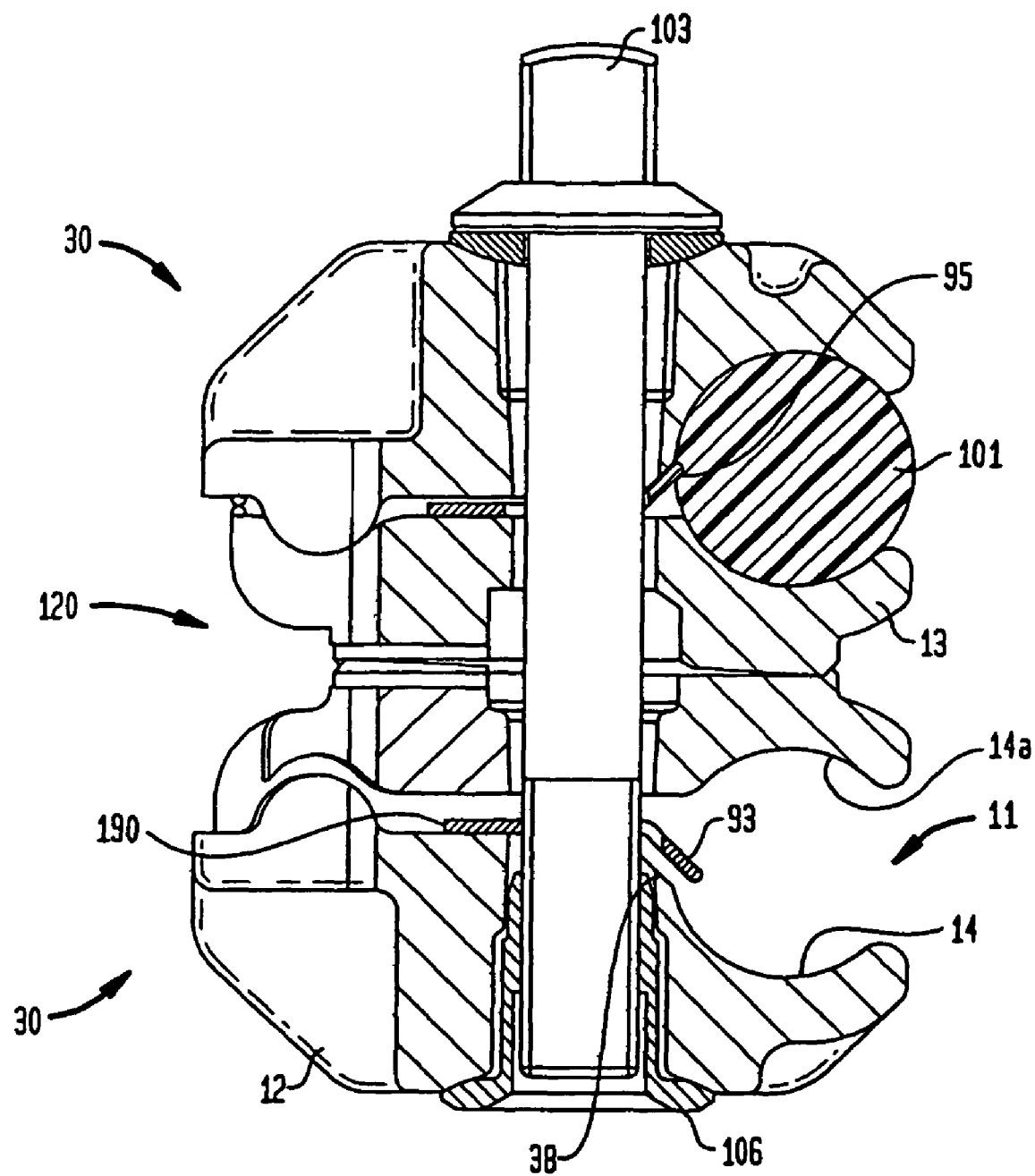
FIG. 24 is a cut side view of the articulated connection according to FIG. 23.

FIG. 23 shows a perspective view of an articulated connection 120 having two clamping elements 30 having inserts 190 according to the sixth exemplary embodiment of the invention, with an inserted rod 101, and FIG. 24 shows a cut side view of this articulated connection 120 according to FIG. 23. The clamping elements 30 correspond to a third embodiment as compared with the clamping elements 10, since they are appropriately modified to accommodate the inserts 190.

In the lower part of FIG. 24, it can be seen that the insert 190 rests on the clamping jaw 12 due to gravity. In this context, the engagement side 93 can rest against the bevel 38 of the clamping jaw 12, but it does not have to do so, because the oblong hole 92 permits a movement of the insert 190 relative to the screw 103. The engagement edge 95 projects into the cavity 11. In this context, engagement edge 95 is oriented approximately centered in height between the clamping jaws 12 and 13. When the rod 101 is inserted by pressing it over the edges of the clamping jaws 12 and 13, as shown in the upper part of FIG. 24, the rod 101 comes to rest in the groove 14. In doing so, it displaces the engagement side 93 towards the edge of the groove 14 and, in particular, against the bevel 38. Then engagement edge 95 engages in the rod 101.

Figure 25:
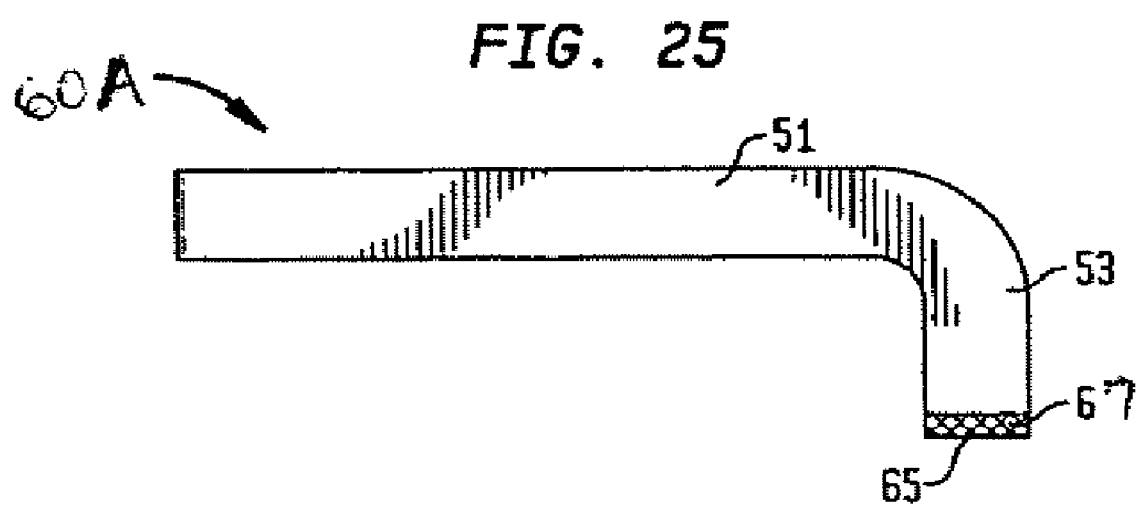
FIG. 25 is a side view of an insert with a roughened surface.

In the case of this variant, as well, the teeth that engage in the rods can be configured in the most various shapes, of which the exemplary embodiment shown form only an advantageous selection. For example, round conical points can also be provided, instead of the teeth 54, 64, 74, 76, 84, in each instance, or in addition to them. They are engagement elements, in each instance. FIG. 25 is a side view of an insert 60A with a roughened surface 67.

In the case of all the exemplary embodiments shown, the insert forms an angled support that directly engages on a rod, with a friction lock. Therefore the clamping elements 10, 20, or 30 are now used only as a guide and spacer part; they are therefore subject to less stress. This permits an even greater material selection for the clamping elements 10, 20, 30. In this context, the insert 50, 60, 70, 80, 90 or 190 engages in the locking element, here 103, 106, on the other side.

The inserts 50, 60, and 70 are shown fitted into a recess 18. This recess 18 can be configured, in particular, in such a manner that inserts 50, 60, and 70 have no play in it, but rather fit into a press fit. They can then not fall out, and form a single-piece unit for the user. The same can also be achieved for the insert 80, by means of a corresponding deformation of the lower clamping jaw 13. As a result, a similar effect as that of the locking bar can also be achieved with reference to the rotation lock, particularly if the insert 90 is configured to be angular rather than round, whereby the characteristics that prevent rotation, for example radial grooves, are provided on the side lying opposite the flat side 86.

Finally, the inserts can also be provided as injection-coated parts in a clamping element.

The exemplary embodiments shown in the drawings, and the characteristics of various exemplary embodiments mentioned in the present description, respectively, should not necessarily be understood as embodiments independent of one another. Instead, it is possible that each characteristic described in one of the exemplary embodiments can be combined with one or more of any other characteristics of other exemplary embodiments, so that other exemplary embodiments result, which are not literally described or shown in the drawings, but lie within the scope of protection claimed in the present claims.

The invention claimed is:

1. A clamping element comprising:
    first and second clamping jaws for clamping a rod-shaped element;
    an axially extending locking element extending through a bore in each of the clamping jaws for providing a clamping force thereon;
    an insert having a first end terminating in an edge surface and a second end, the first end being at a non-90° angle with respect to the second end, for engaging the rod-shaped element, the second end having a bore to receive the locking element;
    the first and second clamping jaws defining a rod-receiving cavity being laterally open, the angled first end of the insert extending into the cavity for engaging the rod-shaped element wherein the first and second clamping jaws lie opposite one another and form the laterally open receiving cavity for lateral accommodation of the rod-shaped element, a gap extending between the first and second clamping jaws, accommodating said second end of the insert, the edge surface being spaced from the first and second jaw and being moveable upon engagement with the rod-shaped element.

2. A clamping element for engaging a rod of an external fixation system, comprising:
    a first jaw member having a bore therethrough and a rod receiving cavity spaced radially from said bore;
    a second jaw member having a bore therethrough and a rod receiving cavity spaced radially from said bore of the second jaw member;
    an axially extending locking shaft extending through the bore of said first and second jaw member for moving said first jaw member towards said second jaw member; and
    an insert having a first part with a bore for receiving said locking shaft and a second part extending into said rod receiving cavity of said first jaw member at a non-90° angle with respect to the first part, said second part having an edge surface for engaging an outer circumferential surface of the rod to be received within said rod receiving cavity of said first jaw member for preventing movement of said rod wherein the rod receiving cavities of the first and second jaw members lie opposite one another and form a combined rod receiving cavity being laterally open for lateral accommodation of the rod, the edge surface being spaced from the first and second jaw members and extends into the combined rod receiving cavity and being moveable upon engagement with the rod.

3. The clamping element according to claim 2, wherein the insert is an angled plate wherein the first part and the second part form an obtuse angle.

4. The clamping element according to claim 2, wherein the insert bore is larger in one direction as compared to a diameter of said locking shaft, so that the insert is moved with respect to the locking shaft when the rod is inserted.

5. A clamping element for engaging a rod of an external fixation system, comprising:
    a first jaw member having a bore therethrough and a rod receiving cavity spaced radially from said bore;
    a second jaw member having a bore therethrough and a rod receiving cavity spaced radially from said bore;
    an axial locking shaft extending along a longitudinal axis through the bore of said first and second jaw member for moving said first jaw member towards said second jaw member; and
    an insert having a first part with a bore for receiving said locking shaft and a second part extending into said rod receiving cavity of said first jaw member at an angle greater than 90° with respect to the first part, said second part having an edge surface extending into a rod receiving cavity of the first jaw member for engaging an outer circumferential surface of the rod to be received within said rod receiving cavity of said first jaw member for preventing movement of said rod, the edge surface being spaced from the first jaw member and being moveable upon engagement with the rod-shaped element.

6. The clamping element as set forth in claim 5 wherein the insert bore is larger in one direction compared to a diameter of the locking shaft so that the insert is moved with respect to the shaft when the rod is inserted.

7. The clamping element as set forth in claim 5 wherein the angle between the first and second insert part is between 120 and 150 degrees.

8. The clamping element as set forth in claim 5 wherein the insert is rectangular with rounded corners.

* * * * *